United States Patent [19]

Hsia et al.

[11] Patent Number: 4,593,021
[45] Date of Patent: Jun. 3, 1986

[54] TREATMENT OF SKIN OVER ANDROGENICITY USING COMPOSITIONS CONTAINING PREGNENOLONE

[75] Inventors: Sung L. Hsia; Walter Voigt; Marty Sawaya; Kathryn Zeoli, all of Miami, Fla.

[73] Assignee: University of Miami, Coral Gables, Fla.

[21] Appl. No.: 641,201

[22] Filed: Aug. 16, 1984

[51] Int. Cl.⁴ .............................................. A61K 31/56
[52] U.S. Cl. .................................................... 514/182
[58] Field of Search ....................... 424/243; 514/182

[56] References Cited

PUBLICATIONS

Merck Index (1976) pp. 1001–1002.
Clinical Research, Apr. 1983, vol. 31, No. 2, an article by Sawaya et al, "Inhibitors of 3β-Hydroxy Steroid Dehydrogenase of Rat Preputial Gland".
Physicians' Desk Reference, 35th edition, p. 838, 1981.

Primary Examiner—Elbert L. Roberts
Attorney, Agent, or Firm—Cushman, Darby & Cushman

[57] ABSTRACT

Disorders of the skin resulting from over androgenicity, such as acne vulgaris, may be treated by applying, to affected areas of the skin, a composition containing a therapeutically effective amount of pregnenolone.

3 Claims, 2 Drawing Figures

TLC OF REFERENCE STEROID

ANDROSTANEDIONE

ANDROSTENEDIONE

DHT
DHA

TESTOSTERONE

ANDROSTANEDIOL
ANDROSTENEDIOL

ORIGIN

TREATMENT OF SKIN OVER ANDROGENICITY USING COMPOSITIONS CONTAINING PREGNENOLONE

FIELD OF THE INVENTION

This invention relates to the prevention of skin disorders caused by over androgenicity of the skin, and in particular to the use of pregnenolone ($\Delta^5$-pregnene-3$\beta$-ol-20-one) to combat or reduce such over androgenicity.

BACKGROUND OF THE INVENTION

Several skin disorders are manifestations of an overreaction of the skin to androgenic stimulation. These include acne vulgaris, seborrhea, hirsutism (undesirable hairiness in women) and male-pattern baldness. Acne vulgaris is especially common among young adults. It is characterized by open and closed comedones, inflammatory papules, pustules, cysts and nodules of the face, chest and back. The disease afflicts primarily the sebaceous gland, which is sensitive to androgenic stimulation, and overreaction of the gland to androgens is an important aspect of the multifactoral pathology of acne. The disease can leave damaging scars, both physically and psychologically.

It is a common clinical observation that acne lesions often flare up or exacerbate when the patient is in a stressful situation. This is the time when the secretion of adrenal cortex is increased in response to stress. The most abundant steroids secreted by the adrenal cortex are dehydroepiandrosterone (DHA) and its sulfate. Although DHA has only weak androgenic activity, studies by the inventor and other laboratories have shown that it is readily metabolized in the skin to form potent androgenic steroids—androstenedione, testosterone and dihydrotestosterone (DHT). These steroids, especially DHT, cause increased sebaceous activity and aggravate acne lesions. Theoretically, it is desirable to arrest the conversion of DHA into these potent androgens in cases of acne vulgaris. In a recent study a significant correlation has been found between the activity of $\Delta^5$-3$\beta$-hydroxysteroid dehydrogenase $\Delta^{4-5}$-isomerase in human sebaceous glands and their secretory activities (Simpson et al, J. Invest. Dermatol. 81:139–144, 1983). This enzymic activity is involved in the first step in the conversion of DHA into more potent androgens.

Presently available remedies for the treatment of acne vulgaris in the acute phase include the following:

Topical antibiotics—erythomycin, clincamycin.

Topical keratolytics—benzoyl peroxide, retinoic acid, sulfur.

Oral antibiotics—tetracycline and derivatives, erythromycin.

Vitamin A and derivatives—Vit. A, 25,000–50,000 Units daily, 13-Cis retinoic acid (Accutane).

Existing remedies for acne all have drawbacks, however. For example, topical application of retinoic acid or benzoyl peroxide irritates the skin and causes the skin to peel. The use of such agents, although effective in treating acne lesions in the acute phase of the disease, causes redness, irritation and undesirable appearance of the skin. The use of antibiotics has the undesirable side effects of changing the microbial environment of the body. The internal use of Accutane alters blood lipids and causes liver toxicity.

Clearly, a substance or composition exhibiting antiandrogenicity and which avoided the problems and drawbacks of the prior art would be useful to those who suffer the conditions resulting from over androgenicity of the skin. Such a composition is the subject of the present invention.

SUMMARY OF THE INVENTION

Figure 1:
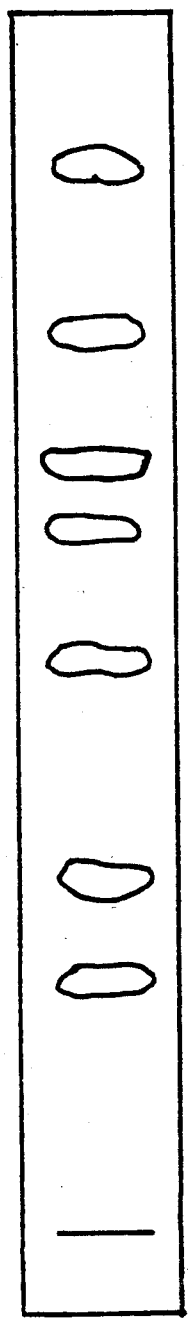
FIG. 1 is a chromatogram showing the chromatographic separation of DHA and its metabolites.

This invention provides a method for the treatment of disorders and conditions resulting from over androgenicity of the skin by topically applying compositions containing therapeutically effective amounts of pregnenolone to areas of the skin in need of such treatment. The invention further provides compositions useful for the treatment of conditions resulting from over androgenicity of the skin, said compositions comprising a pharmaceutically acceptable carrier containing a therapeutically effective amount of pregnenolone.

Pregnenolone is a naturally occurring steroid having the following formula

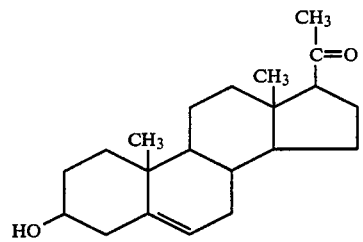

Pregnenolone is an intermediate in the biosynthesis of progesterone and corticosteroids. It has no known hormonal activity of its own, however.

The present invention results from the determination that pregnenolone is an inhibitor for the enzyme 3$\beta$-hydroxysteroid dehydrogenase $\Delta^{4-5}$-isomerase (3$\beta$HSD). This inhibitory activity is the basis for the antiandrogenic activity of pregnenolone. 3$\beta$HSD is the enzyme which converts the weakly androgenic adrenal steroid DHA into the more potent androgen androstenedione, which in turn forms testosterone and DHT in the skin. These metabolites of DHA are thought to cause over androgenicity.

Thus, by effectively inhibiting 3 $\beta$HSD over androgenicity may be effectively prevented or reduced.

It is an object of this invention to provide compositions and methods for combatting and reducing over androgenicity of the skin.

It is further an object of this invention to provide compositions and methods for combatting and reducing conditions and disorders which result from over androgenicity of the skin.

It is further an object of this invention to provide compositions and methods for combatting and reducing over androgenicity of the skin, which compositions and methods avoid the problems of the prior art.

These and other objects and advantages of the invention will become more apparent and more readily appreciated from the following detailed description of presently preferred exemplary embodiments of the invention.

DETAILED DISCUSSION

To assess the androgen inhibiting activity of pregnenolone, rat preputial gland was employed to investigate the in vitro androgenic action of DHA. Growth of the gland has been shown to respond to the stimulation of androgenic, but not estrogenic or adrenocortical steroids (Huggins et al, Endocrinology, 57, 35–32, 1955). A pair of the glands are situated in the prepuce of the rat of either sex weighing between 125–200 mg in an average 200 g rat, being slightly larger in the male animal. The animals employed were female Sprague-Dawley rats, 10–12 weeks old and weighing 225–300 g.

The experimental format, stated broadly, was to excise preputial glands from rats and prepare a homogenate therefrom. A predetermined amount of homogenate (the sample) was then spiked with radiolabeled (with $^3$H) DHA, in the presence or absence of pregnenolone, and the sample was incubated. The sample was then extracted to recover steroid (i.e. DHA plus metabolites) and the DHA and metabolites were separated using thin layer chromatography. The metabolites were quantitated by removal from the thin layer plate and counting in a scintillation counter. By determining the extent of metabolite formation, the extent of inhibition of 3$\beta$HSD could be correspondingly determined.

To obtain the preputial glands, female rats (unless specified otherwise) were sacrificed by one of 3 methods: an overdose of ether, injection with Nembutol Sodium Solution (0.4 ml) intraperitoneally, or a blow behind the head, and the glands were excised and weighed. The approximate weights of a pair of glands were 125–175 mg from the adult female rat and 150–200 mg from the male rat.

Satisfactory homogenization was achieved by brief grinding of minced preputial glands in 0.1M Tris buffer with a Polytron homogenizer, type PT 10-ST (Kinematica, Gmbh., Luzern, Switzerland) with the voltage control at 3–5 for about 30 seconds; an alternative procedure was to use a motor driven Ten Broeck all glass tissue homogenizer. The entire procedure was carried out below 4° C. The latter method was used for the homogenation of isolated cells in Bands I-V, in 0.1M citrate-phosphate buffer, pH 7.4 (Hsia et al, J. Steroid Biochem, 19:599–605 (1983)).

Experiments were initially conducted to ensure that DHA and its metabolites could be separated chromatographically. The chromatographic procedure was conducted on thin layer plates prepared with Silica gel H on glass plates 5 cm wide and 40 cm long, thickness ⅜ mm. Plates were activated at 80° for 30–60 minutes and developed in a solvent system of dichloromethane:ethyl acetate (4:1, v/v). After 18 hours of development at room temperature, the carrier $\Delta^4$-3-keto (metabolites were primarily androstenedione, with minor amounts of testosterone) steroids were visualized by UV light, and the others by exposure to iodine vapor. According to the method of Matthews et al (1962), when placing the developed plate into iodine vapors for a few minutes, the formerly invisible spots of steroids turn yellow or yellowish brown. The position of the steroid can be readily traced with this method. The excess of iodine can be removed from the layer easily with a current of warm air (30° to 50° C.) and thus the $C_{19}$ steroids will not decompose during the course of detection. Elution and quantitative evaluation of steroids can be effected after removal of the iodine. The steroids having a 3-keto-4-ene and 5-ene-7-keto structure absorb Ultraviolet light absorption of 240 m$\mu$ wavelength and, when illuminated with UV light, a brownish red spot appears at the site of the steroids on either alumina or silica-gel thin layer plates. For quantitation the plates were then scraped in 1 cm sections for radioassay of $^3$H in a Packard Tri-Carb liquid scintillation counter. Silica gel H blanks and $^3$H-standards (Packard Instrument Co.) were also counted. This TLC system using long plates clearly separated the reference steroids (FIG. 1). The mobilities of the steroids after 18 hours of development were as follows: androstenediol, 7–9 cm; androstanediol, 10–12 cm; testosterone, 17–19 cm; DHA, 21–23 cm; DHT, 23–25 cm; androstenedione, 27–29 cm/ and androstanedione 32–34 cm. These TLC systems clearly demonstrated that DHA and its metabolites can be separated chromatographically.

Steroid metabolizing activities were determined by incubating the homogenates with 1,2-$^3$H-DHA ($10^6$ dpm) diluted with 100 nmoles of non-radioactive DHA. The steroid substrate was dissolved in ethanol, and an aliquot of 10 $\mu$l was added to the preputial gland homogenate equivalent to 2 mg of protein. NAD, NADH, and NADPH-generating systems were also included.

The mixture was incubated and shaken at 37° C. for a predetermined time, and the incubation was terminated by immersing the incubation tube in a dry ice-acetone bath, followed by lyophilization. Carrier steroids, approximately 100 $\mu$g each of testosterone, DHT, and androstenedione, androstanedione, androstanediol, androstenediol, and DHA were then added, and the mixture was repeatedly extracted with ethanol. The carrier steroids were non-radioactive steroids added to allow detection of DHA and its metabolites under UV light following the chromatographic procedure described above. The extract was concentrated under a stream of $N_2$ gas and the residue applied to thin layer plates for chromatographic separation. The recovery of $^3$H by this procedure, based on measured radioactivity was >95%.

The percentage of DHA substrate converted to product was calculated as:

$$\frac{\text{Radioactivity in Product Peak}}{\text{Total Radioactivity Chromatographed}} \times 100\%.$$

The amount of product was then calculated from nmoles substrate originally added times percentage of radioactivity in product peak.

The inhibitory activity of pregnenolone on the 3$\beta$HSD for DHA was calculated from the amount of radioactive androstenedione formed in the presence and absence of pregnenolone and was expressed as a percentage of the total amount of $\Delta^4$-3-keto product (mainly androstendione plus a small amount of testosterone) formed in the absence of the inhibitor. Four separate incubations resulted in a range of inhibition of 91–92% for pregnenolone.

The effects of hormones and hormonally active substances on sebaceous glands can also be evaluated using the Syrian hamster flank organs as an animal model. The results of experiments using hamsters are valuable inasmuch as they can provide in vivo confirmation of the in vitro experiments like those described above using rat preputial gland. The flank organs, also called the costovertebral spot or the costovertebral organ, are sebaceous structures located on each flank of the animal. Like the sebaceous glands of the human and the preputial gland of the rat they are androgen dependent (Voigt and Hsia, 1973; Gomez and Frost, 1969; Frost and Gomez, 1973).

The organ in the mature male hamster measures approximately 8 mm in diameter, is heavily pigmented and is covered with coarse dark hairs (Voigt and Hsia, 1973). The organ of the female animal is undeveloped, measuring about 2 mm in diameter, lightly pigmented, without dark hairs, and is at times difficult to see. The anatomical and histological changes in this organ in response to androgens have been described by Hamilton and Montagna (1950).

Hamster flank organs have been documented as indicators of androgenic activity. Frost and Gomez (1973) tested the response of the flank organ of female hamsters to graded doses of testosterone, dihydrotestosterone, methyltestosterone, $\Delta^4$-androstenedione, androsterone, epiandrosterone, and progesterone. The results of topical application (5 days/week for 2 weeks) showed a unilateral stimulation of sebaceous gland growth and pigmentation for the following steroids: testosterone, DHT, methyltestosterone, androstenedione. The other compounds tested, androsterone, epiandrosterone and progesterone did not cause flank organ growth or increased pigmentation when applied topically. Further investigations by these authors did not, however, concern the androgenic potential of DHA in stimulating female hamster flank organs.

Before testing the anti-androgenic properties of pregnenolone on hamster flank organs and relying on the results, a centrally important question therefore needed to be answered—Could DHA be shown to stimulate growth in the flank organs? This question was answered by applying graded doses of DHA, 12 $\mu$g, 60 $\mu$g, 120 $\mu$g to the right side of female hamsters (5 hamsters/group), for 7 days/week for 6 weeks. Results showed not only a local stimulation, but stimulation of both flank organs, hence systemic stimulation.

Hamster flank organs were accordingly used to test in vivo the androgenic inhibitory properties of pregnenolone.

Female Syrian Golden Hamsters were used in this experiment. All hamsters were maximally stimulated with DHA (120 $\mu$g/0.1 ml acetone) applied to the right flank organ each day for 4 weeks. Similarly the left side was treated with acetone. Hamsters were then separated into two groups 1. Control—where no topical inhibitor was applied to the maximally stimulated organs.

2. Pregnenolone treated—pregnenolone was applied topically (1200 $\mu$g/0.1 ml acetone) to each (left and right) maximally stimulated flank organ for 3 days.

On the afternoon of day 3, an intracardial injection of 1,2-$^3$H-DHA 5 $\mu$Ci/0.1 ml saline buffer solution) was given to both experimental groups anesthetized with ether. One hour following the injection, the hamsters were killed, flank organs (left and right) excised, then placed in liquid $N_2$ and weighed. Each organ was then placed in a 16 mm $\times$ 150 mm test tube containing methanol and was homogenized, extracted and analyzed for steroid metabolites by separating the metabolites using thin layer chromatography as described above, scraping the thus separated metabolites from the thin layer plates, and quantitating using a scintillation counter. Calculations were made as previously shown.

Figure 2:
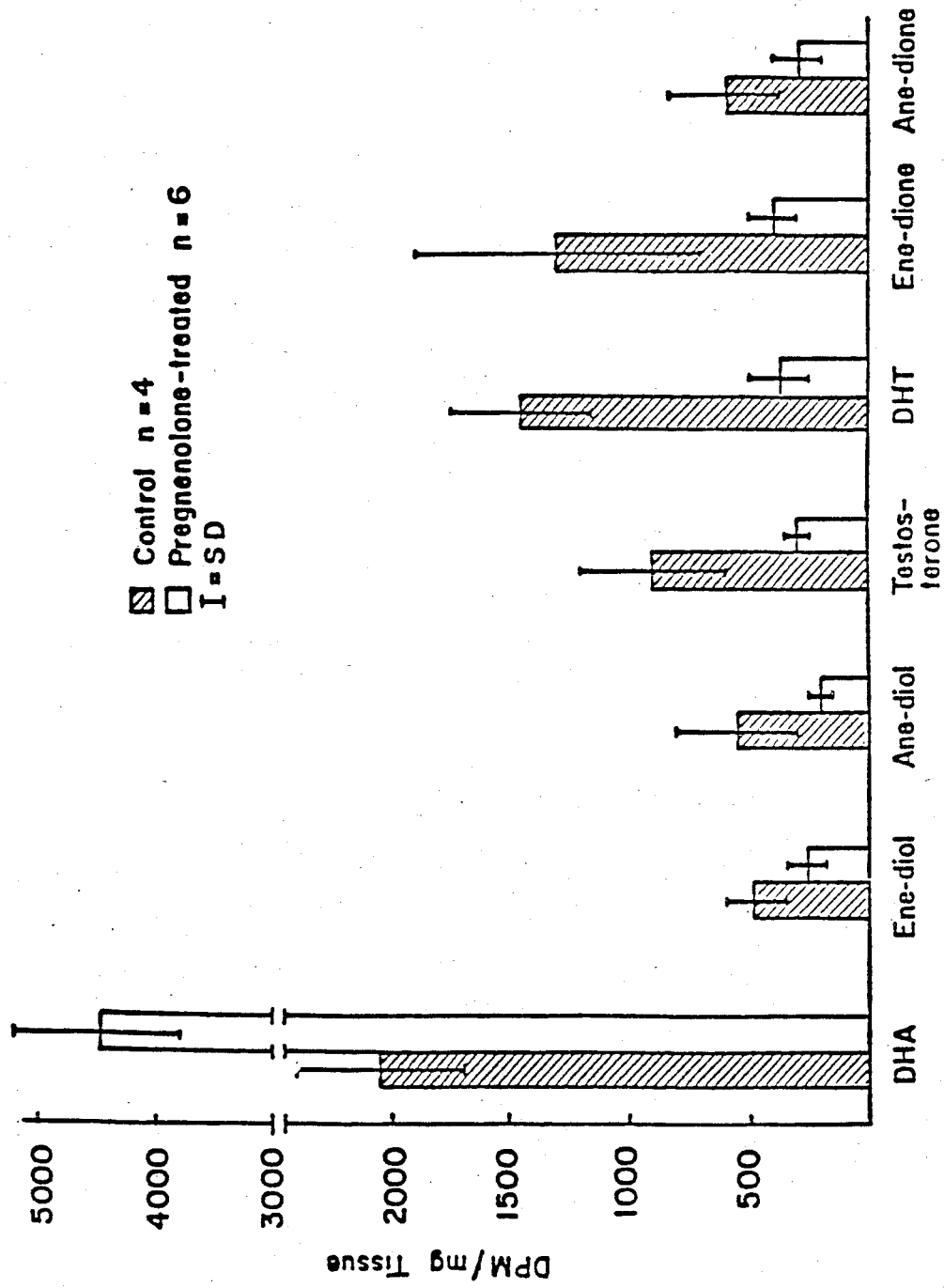
FIG. 2 is a graphical representation of $^3$H-DHA in flank organs of female hamsters treated with and without pregnenolone.

Results are shown in FIG. 2 expressed as DPM/mg tissue.

Results revealed that the inhibitor effect of pregnenolone on the 3$\beta$HSD of DHA previously observed in preputial gland microsomes was also seen in this in vivo experiment. Significant differences ($P<0.01$) were seen in the total metabolites converted from 1,2-$^3$H-DHA in the hamsters receiving topical application of pregnenolone versus those in the control group, not receiving topical inhibitor.

Control hamsters, not treated with inhibitor, show greater formation of testosterone, DHT and androstanediol than the hamsters treated for 3 days previously with pregnenolone.

The above experiments conclusively establish that pregnenolone exhibits potent anti-androgenic activity.

With regard to formulation for use with humans, because pregnenolone is insoluble in water, most aqueous base vehicles or carriers are not useful in the invention. Vehicles with a high content of alcohols, such as isopropanol or mixtures of alcohols with longer ($C_4$–$C_{10}$) alkane or alkene chains, in which pregnenolone is soluble, would afford a suitable base for the formulation as liquid, gel or cream. Glycerol may be added in the preparation as an emollient. Glycerol is hygroscopic; it keeps the skin surface from drying. Other additions of moisturizers or perfumes as known in the art are compatible with pregnenolone.

The useful range of pregnenolone concentration effective for use in human topical application ranges between about 0.1%, based on the weight of whatever pregnenolone-containing composition is being employed, and an upper limit governed only by the solubility of pregnenolone in the particular solvent or carrier. It is noted that at lower concentrations the therapeutic benefits become drawn out and more gradual over a longer period of time.

Clinical trials have also been conducted which indicate that compositions containing pregnenolone exhibit a high level of efficacy and acceptability to patients suffering from conditions and disorders resulting from over androgenic skin conditions. The following experiment was conducted and is a typical trial.

In a double-blind clinical trial 23 patients with acne vulgaris volunteered to participate. Fifteen patients (11 females and 4 males) were given a 1% solution of pregnenolone dissolved in isopropanol containing 1% glycerol, and 8 patients (5 females and 3 males) were given a 1% solution of glycerol in isopropanol. Neither the patients nor the attending dermatologist knew whether or not the dispensed solution contained pregnenolone. The patients were instructed to stop using their previous medications for two weeks and then to apply the given solution to their faces twice daily. They were reexamined biweekly.

After twelve weeks of treatment, 5 patients (33%) of the group treated with 1% pregnenolone in isopropanol containing 1% glycerol, noted definite improvement, with reduction in the size and number of lesions. Four patients (26%) noted slight reduction of the number of lesions and a reduction in the oiliness of the skin; 2 patients (13%) noted reduction of oiliness, and 4 patients (26%) noted no change in lesions or oiliness. Some of the patients observed that the pores in their skin had reduced in size and consequently, the skin felt smoother. In particular, two patients showed marked reductions in skin oiliness and in pore size, resulting in a rather dramatic overall improvement in the appearance of their skin.

It is noted that the methods and compositions disclosed herein generally result in some noticeable reduction in oiliness, oiliness being one of the primary manifestations of skin over androgenicity in general, and seborrhea in particular.

Of the group treated with 1% glycerol in isopropanol, 1 patient (13%) noted a slight decrease in the number of lesions, 6 patients (75%) noted no change and 1 patient (13%) noted an increase in the number of lesions.

The above trial provides strong evidence that pregnenolone has a beneficial effect in the treatment of acne, and that continued use of pregnenolone prevents the development of new lesions. There has been no complaint of irritation or discomfort caused by the topical application of pregnenolone.

A number of the patients who took part in the clinical trial had used other medications previously. They claim that pregnenolone was more effective and more acceptable to them. Had they been successfully treated by previous therapy, they would not have volunteered to participate in the clinical trial with pregnenolone. The fact that they obtained good results with pregnenolone is evidence that pregnenolone is more effective and more acceptable.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method of treating acne vulgaris resulting from over androgenicity of the skin, comprising topically applying a therapeutically effective amount of pregnenolone to the acne-containing areas of the skin of a person in need of such treatment.

2. The method of claim 1, wherein said pregnenolone is applied as a composition comprising said pregnenolone and a pharmaceutically acceptable carrier.

3. The method of claim 2, wherein said pregnenolone is present in said composition in an amount of at least about 0.1 wt. % based on the composition.

* * * * *